(12) United States Patent
Zohmann

(10) Patent No.: US 6,558,353 B2
(45) Date of Patent: May 6, 2003

(54) SPINAL NEEDLE

(76) Inventor: Walter A. Zohmann, 528 Park Ave., Park City, UT (US) 84068

( * ) Notice: Subject to any disclaimer, the term of this patent is extended or adjusted under 35 U.S.C. 154(b) by 50 days.

(21) Appl. No.: 09/769,630

(22) Filed: Jan. 25, 2001

(65) Prior Publication Data
US 2002/0099335 A1 Jul. 25, 2002

(51) Int. Cl.[7] .............................................. A61M 5/178
(52) U.S. Cl. .................. 604/158; 604/161; 604/164.01; 604/164.07; 604/168.01; 604/170.02; 606/167; 606/186
(58) Field of Search ................................ 604/158, 161, 604/164.01, 164.07, 168.01, 170.02; 606/167, 184, 185, 186

(56) References Cited

U.S. PATENT DOCUMENTS

| | | | | |
|---|---|---|---|---|
| 2,922,420 A | * | 1/1960 | Cheng | 128/221 |
| 3,565,074 A | * | 2/1971 | Foti | 128/214.4 |
| 3,856,009 A | * | 12/1974 | Winnie | 128/214.4 |
| 4,230,123 A | * | 10/1980 | Hawkins, Jr. | 128/658 |
| 4,308,875 A | * | 1/1982 | Young | 128/753 |
| 4,317,445 A | * | 3/1982 | Robinson | 128/214.4 |
| 4,629,450 A | * | 12/1986 | Suzuki et al. | 604/164 |
| 4,973,313 A | * | 11/1990 | Katsaros et al. | 604/165 |
| 4,994,036 A | * | 2/1991 | Biscoping et al. | 604/158 |
| 5,106,376 A | * | 4/1992 | Mononen et al. | 604/164 |
| 5,242,410 A | * | 9/1993 | Melker | 604/164 |
| 5,250,035 A | * | 10/1993 | Smith et al. | 604/164 |
| 5,304,141 A | * | 4/1994 | Johnson et al. | 604/158 |
| 5,312,360 A | * | 5/1994 | Behl | 604/164 |
| 5,336,191 A | * | 8/1994 | Davis et al. | 604/165 |
| 5,466,225 A | * | 11/1995 | Davis et al. | 604/165 |
| 5,480,389 A | * | 1/1996 | McWha et al. | 604/165 |
| 5,571,091 A | * | 11/1996 | McWha | 604/158 |
| 5,628,734 A | * | 5/1997 | Hatfalvi | 604/272 |
| 5,669,882 A | * | 9/1997 | Pyles | 604/164 |
| 5,730,749 A | * | 3/1998 | Battenfield | 606/167 |
| 5,800,445 A | * | 9/1998 | Ratcliff et al. | 606/116 |
| 5,836,914 A | * | 11/1998 | Houghton | 604/117 |
| 5,865,806 A | * | 2/1999 | Howell | 604/164 |
| 5,871,470 A | * | 2/1999 | McWha | 604/158 |
| 6,245,044 B1 | * | 6/2001 | Daw et al. | 604/158 |

* cited by examiner

Primary Examiner—David A. Scherbel
Assistant Examiner—Frederick C. Nicolas
(74) Attorney, Agent, or Firm—Kirton & McConkie; Michael F. Krieger

(57) ABSTRACT

The present invention is directed toward an improved spinal needle. A needle hub is disposed about a proximate end of a hollow needle. The needle hub side port indicators provide visual and tactual verification by a user of the orientation of the side port on the needle. The needle hub also includes a window with a magnified view. The invention provides a stylet cap disposed about a proximate end of a stylet that freely slides inside the hollow needle and needle hub. The stylet cap forms a pressure fit with the needle hub, and can be engaged in the pressure fit from any axial orientation.

17 Claims, 5 Drawing Sheets

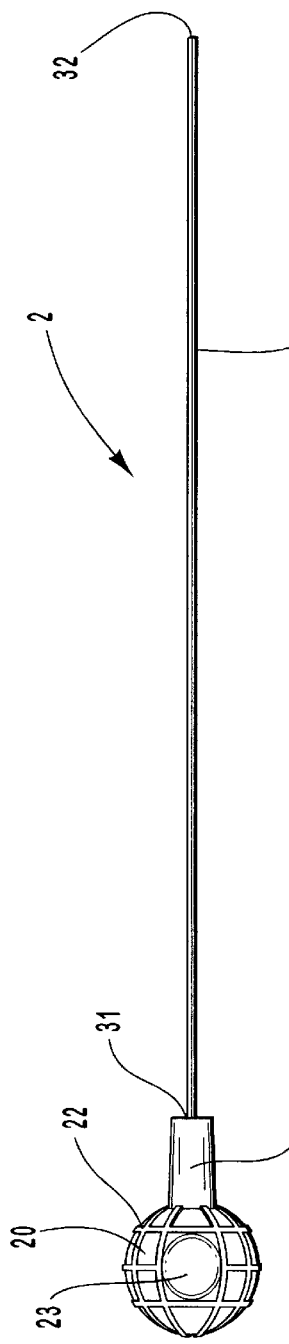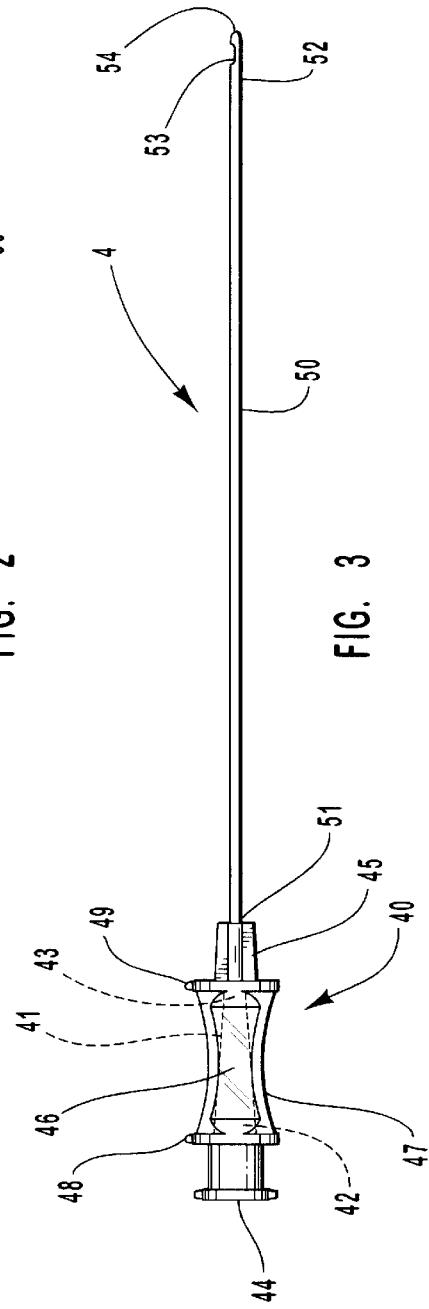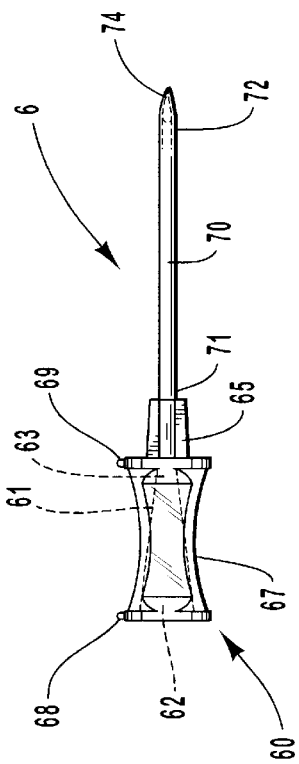

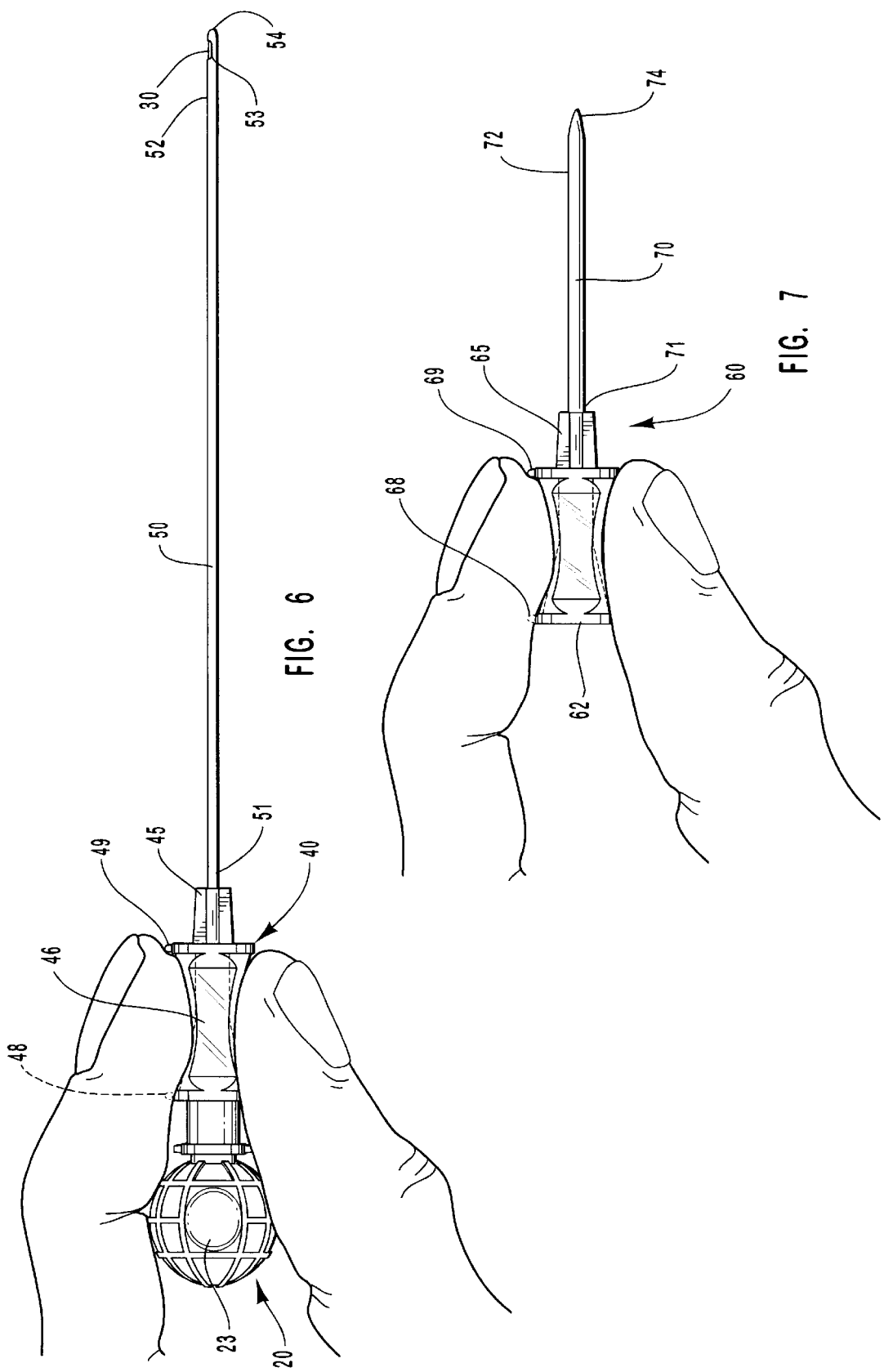

SPINAL NEEDLE

BACKGROUND

1. Field of the Invention

This invention relates to innovative needles for facilitating lumbar puncture procedures generally and, more particularly, to a novel, atraumatic needle apparatus and method for reducing loss of cerebral spinal fluid (CSF) during such procedures.

2. Background

Spinal anesthesia is one of the most frequently employed methods of regional anesthesia. This regional anesthesia is accomplished by the temporary interruption of nerve transmission using a local anesthetic injected into the readily identifiable subarachnoid space. The ensuing anesthesia is predictable, occurs rapidly, and is associated with profound muscle relaxation. The patient may be wide awake, or if preferred, the anesthetic may be supplemented with varying amounts of sedative-tranquilizers. Spinal anesthesia is particularly useful for surgery involving the lower extremities, pelvis, perineum, and lower abdomen.

The spinal column, which surrounds the spinal cord, is formed by a series of vertebrae separated by cartilaginous intervertebral disks and united by a series of ligaments. The body of each vertebra bears the weight of the patient and forms the base of the neural arch. The arch, which surrounds the spinal cord, is made up of a pedicle and lamina on each side. Between the laminae of each vertebra there is a posterior opening in the vertebral canal. It is through this opening that a spinal needle is passed when performing a subarachnoid block.

In adults the spinal cord varies in length from 40 to 45 cm. and ends at various levels of the vertebral column depending on the age of the patient. In the newborn, the spinal cord extends to the third lumbar vertebra, but in the adult it usually ends at the lower border of the first lumbar vertebra because the spinal cord does not grow as much as the vertebral column. Thirty-one pairs of symmetrically arranged spinal nerves are each attached to the spinal cord by an anterior and posterior root. Because the spinal cord is shorter than the vertebral column, the spinal cord segments in adults do not lie opposite their corresponding vertebrae. The spinal nerve roots must travel obliquely in a caudad direction to reach their respective intervertebral foramina. The roots of the lumbar, sacral, and coccygeal nerves comprise the cauda equina and are necessarily the largest and longest in order to reach their intervertebral foramen. The greater size of these nerve roots provides a larger surface area to be exposed to the action of local anesthetics, thus allowing more rapid onset of anesthesia.

The spinal cord is covered by three membranes or meninges. The dura mater (the outermost membrane) is the downward continuation of the meningeal layer of the cranial dura mater. The middle of the three coverings, the arachnoid is a thin membrane closely adherent to the dura mater. The dura and the arachnoid are in such close contact that usually it is not possible to puncture the dura without also piercing the arachnoid. Nevertheless, on rare occasions, the tip of the conventional epidural or spinal needle may accidentally enter the subdural space. Local anesthetic inadvertently injected into the subdural space will diffuse poorly and result in inadequate contact with the nerve roots. Poor or absent anesthesia may ensue. Should subdural placement occur during an attempted epidural anesthetic, the improper position of the needle may not be recognized and the injection of an epidural dose of local anesthetic may result in a much higher block than anticipated.

The innermost membrane, the pia mater, is a thin, delicate, highly vascular membrane closely adherent to the spinal cord. The space surrounding the pia is filled with cerebrospinal fluid and is enclosed externally by the arachnoid. In addition to spinal fluid, this space contains the spinal nerve roots and the main blood vessels of the central nervous system. In the cervical and thoracic regions, the space is only about 3 mm deep, but below the lower border of the first lumbar vertebra, where the spinal cord usually ends, the space has a diameter of about 14 to 15 mm.

A typical spinal anesthetic delivery device comprises three components. A sharp, hollow introducer component a few centimeters in length that is used to puncture the skin, a more blunt hollow needle component several centimeters in length that is slideably disposed within the hollow introducer to allow the caregiver to delicately pierce the dura membrane, and a stylet component that is slideably disposed within the needle to selectively occlude the needle and control the flow of fluid therein. The introducer and needle components both have hubs on their proximate ends. The hubs act as handles or grips to facilitate manipulation of the introducer and needle.

Delivering spinal anesthesia may be accomplished using a lumbar puncture procedure. The lumbar puncture generally involves the following steps:

(1) Placing the patient receiving the procedure in the lateral decubitus position on the edge of the bed with the patient's back exposed to the caregiver carrying out the procedure;

(2) Placing the patient in a fetal like position with the head supported so that the head and spine are parallel to the bed and the knees are to the chest;

(3) Marking the posterior iliac crest and palpate the L4 spinous process;

(4) Anesthetizing the patient's skin in preparation for inserting an introducer and spinal needle;

(5) Inserting the introducer at the marked puncture point;

(6) Advancing the needle slowly through the introducer until the dura membrane is breached. A distinct "pop" may be heard when the membrane is pierced. The needle should be inserted approximately two centimeters into the skin.

(7) After the dura membrane is pierced, withdrawing the stylet disposed within the needle as the needle is advanced to verify the presence of CSF flowing back out of the needle;

(8) Injecting the anesthetic through the needle to induce the anesthetic block;

(9) Withdrawing the needle and introducer without replacing the stylet; and

(10) Dressing the puncture site with a bandage.

A spinal needle 9 cm long is usually adequate for lumbar puncture, but longer ones (10–15 cm) are available for the occasional obese patient or difficult paramedian approach. The removable, close-fitting stylet helps stiffen the needle and prevents coring of the tissue. Commonly, two sizes of spinal needles are used, 22–27 gauge. The larger diameter 22 gauge needle is easier to direct and renders the characteristic feel of the various ligaments penetrated easier to appreciate. However, the incidence of postspinal headache is increased with the larger needle, particularly if the larger needle is also equipped with a standard point which is a cutting bevel.

A postdural puncture headache is the most common postoperative complication of spinal anesthesia. The incidence increases with the larger spinal needles and those with a cutting bevel at the tip but decreases with increasing patient age. Postdural puncture headache also occurs more commonly in women than in men, and more often in pregnant women than in nonpregnant women. The headache is positional in that it comes on in the upright position and is relieved or at least improved in the recumbent position.

The causative mechanism of the postdural puncture headache is believed to be associated with the continuing leakage of cerebrospinal fluid (CSF) through the dural opening left by the spinal needle. The leakage of CSF causes a decrease in CSF pressure which, in turn, produces compensatory cerebral vasodilation. Bringing the patient into the erect position also results in traction on the pain-sensitive, dilated blood vessels. Accordingly, conservative therapy for the postdural puncture headache consists of bed rest and analgesics.

Various preventive measures for the postdural puncture headache have been advocated. The common practice of keeping the patient supine for 4 to 24 hours after lumbar puncture has been shown to be ineffective. For a standard point needle having a cutting bevel at its tip, insertion of the needle with the bevel parallel to the longitudinal fibers of the dura appears to produce a smaller rent in the dura with a lower incidence of headache. Pencil point needles such as the commercially available Whitacre and Sprotte needles also have a lower incidence of headaches. These pencilpoint needles have a closed pencil point created when the open end of the needle is swaged closed, as the name implies, like a pencil point or, more accurately, with a conical apex. This conical apex is believed to spread, rather than cut, the predominately longitudinal dural fibers and, on removal of the needle, the resulting dural hole should be smaller and seal off more rapidly. Indeed, studies have shown that the incidence of postspinal headache when a 22 gauge conical apex needle is used is comparable to that following use of the much smaller 26 gauge, bevel needle.

In an attempt to minimize leakage of CSF, an available procedure is to create what is known as a blood patch. This is done by obtaining 10 to 20 cc of blood from the patient and injecting this volume of blood into the tissue adjacent the puncture site of the spinal needle. This relatively large volume of blood is required since it is virtually impossible for the health care professional to exactly position the blood patch directly over the original puncture site. In effect, therefore, the blood patch is designed to seal the dural puncture thereby significantly minimizing the frequency of the postdural headache.

Another disadvantage to the presently available pencilpoint-tip spinal needles is that the sides of the tip are generally straight in a true cone configuration. Thus, a relatively abrupt shoulder is formed as a ridge at the juncture between the sloped sides of the conical tip and the cylindrical side walls of the body of the needle. It is currently postulated that this relatively abrupt change in the profile of the needle excessively distorts the dura and thereby contributes to the presence of a post puncture hole in the dura.

Once the needle has punctured the dura, excessive movement of the needle may undesirably increase the size of the puncture hole of further traumatize surrounding tissue. For example, if the needle side port is improperly positioned because the caregiver was unable to accurately gauge the orientation of the sideport, during insertion, the caregiver may attempt to rotate and adjust the needle to properly position the side port to deliver the drug. This additional movement may undesirably increase the size of the dura puncture hole or increase trauma to the tissue. Likewise, if the caregiver is unable to see whether there has been a return of CSF or some other fluid into the needle hub, the care giver may have to move or reposition the needle in order to verify CSF return or the pressure of the fluid. Moreover, if the stylet is difficult to handle or troublesome to secure in place, excessive manipulation of the stylet can cause unnecessary displacement of the needle resulting in additional trauma to the dura and increasing the size of the dura puncture hole.

It would be advantageous to provide an improved needle for facilitating lumbar puncture procedures and for reducing the likelihood of undesired CSF leakage caused by unintended enlargement the lumbar puncture hole or trauma to surrounding tissue. It would further be and advantage to provide a needle for facilitating lumbar puncture whereby the orientation of the side port is easily verified, the return of the CSF is readily visible through the needle hub and the stylet is easily inserted and manipulated.

SUMMARY AND OBJECTS OF THE INVENTION

This invention is an improved needle for facilitating lumbar puncture procedures. More particularly, the invention is a novel, atraumatic needle apparatus for reducing loss of CSF through the dura puncture hole. The apparatus comprises a sharp, hollow introducer component a few centimeters in length that is used to puncture the skin, having raised tip indicators disposed upon the introducer hub; a more blunt, hollow needle component several centimeters in length that is slideably disposed within the hollow introducer, the needle hub having raised side port indicators and a magnifying window for viewing the return of fluid in the hub; and a stylet component that is slideably disposed within the hollow needle to selectively occlude the needle and control the flow of fluid therein. The introducer and needle components both have relatively small transparent hubs on their proximate ends. The hubs act as handles or grips to facilitate manipulation of the introducer and needle and allow the caregiver to view fluids passing into or out of them.

It is, therefore, a primary object of this invention to provide improvements in spinal needle apparatus.

Another object of this invention is to provide a spinal needle apparatus with means for visually and tactually verifying the orientation of the needle side port.

It is yet another object of one embodiment of the present invention to provide a spinal needle apparatus with means for facilitating visual verification of CSF return.

It is yet another object of one embodiment of the present invention to provide a spinal needle apparatus having a stylet that is easily inserted and manipulated.

These and other objects and features of the present invention will become more readily apparent from the following description in which preferred and other embodiments of the invention have been set forth in conjunction with the accompanying drawing and appended claims.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

FIG. 2 shows a side view of the stylet

FIG. 3 shows a side view of the needle component

FIG. 4 shows a side view of the introducer without the sheath

FIG. 6 shows the needle hub with the user's finger in contact with the raised portions for verifying the orientation of the side port;

FIG. 7 shows the introducer hub with the user's finger in contact with the raised portions for verifying the orientation of the beveled tip.

DETAILED DESCRIPTION OF THE PREFERRED EMBODIMENTS

It will be readily understood that the components of the present invention, as generally described and illustrated in the figures herein, could be arranged and designed in a wide variety of different configurations. Thus, the following more detailed description of the embodiments of the system and method of the present invention, and represented in FIGS. 1 through 8, is not intended to limit the scope of the invention, as claimed, but is merely representative of the presently preferred embodiments of the invention.

The presently preferred embodiments of the invention will be best understood by reference to the drawings, wherein like parts are designated by like numerals throughout.

Figure 1:
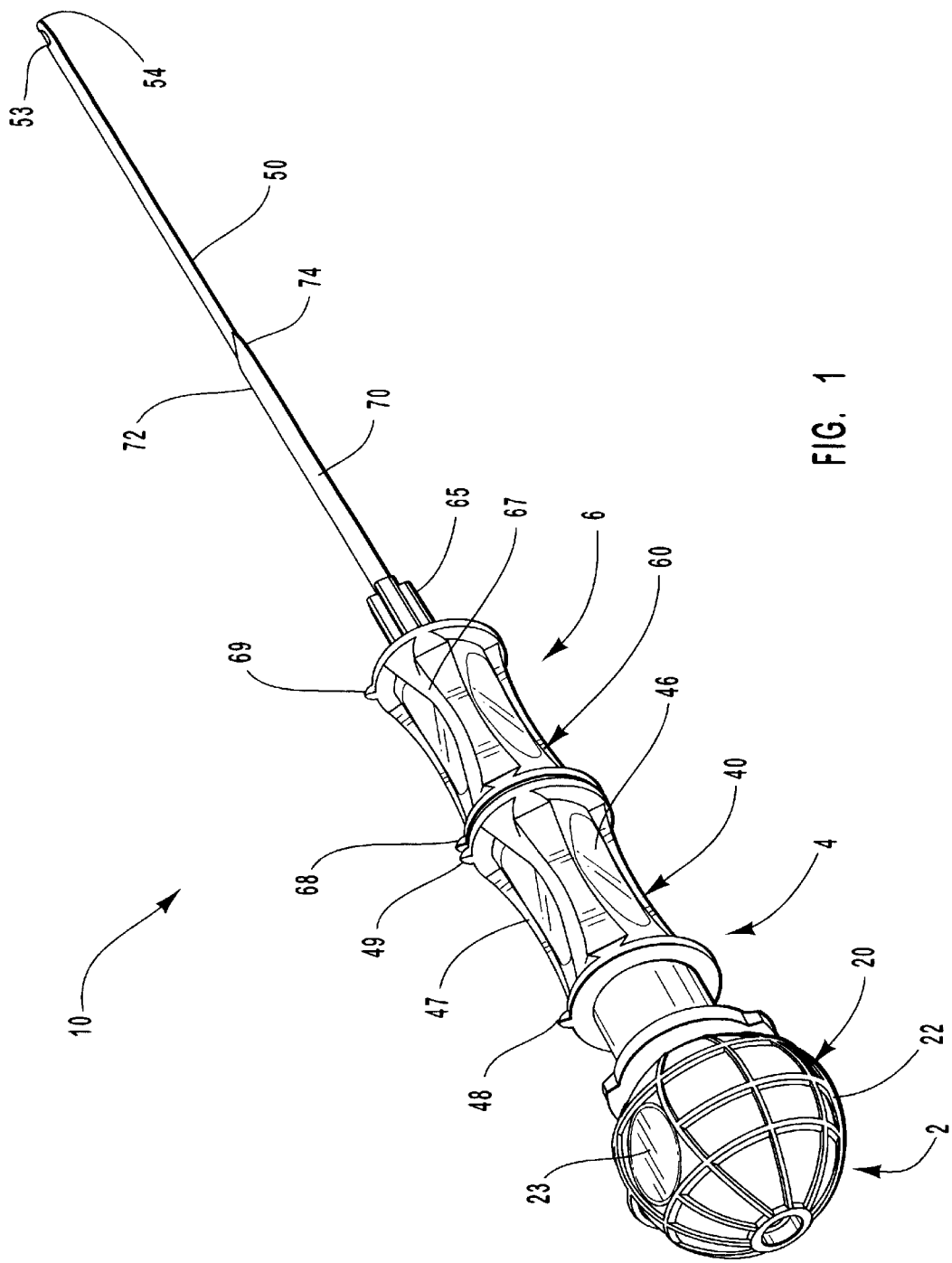
FIG. 1 shows a perspective of the needle apparatus.

The present invention relates to an improved spinal anesthesia needle apparatus. As shown in FIG. 1, a spinal anesthesia needle apparatus 10 comprises three main components: a stylet component 2 further comprising a stylet cap 20 and stylet 30; a needle component 4 further comprising a needle hub 40 and a hollow needle 50; and an introducer component 6 further comprising an introducer hub 60 and hollow introducer 70.

As shown in FIG. 2, stylet component 2 comprises stylet 30 having a proximate end 31 and a distal end 32. The term proximate as used herein connotes proximate to the "main body" of needle apparatus 10, or in other words, nearer the portion of needle apparatus 10 that connects to a syringe. The term "distal" connotes a position removed from the main body of needle apparatus 10 or in other words, nearer the tip of needle apparatus 10. Stylet 30 has a diameter and a length. The length and diameter of stylet 30 are sufficient to occlude hollow needle 50 when stylet 30 is inserted into needle 50.

Figure 5:
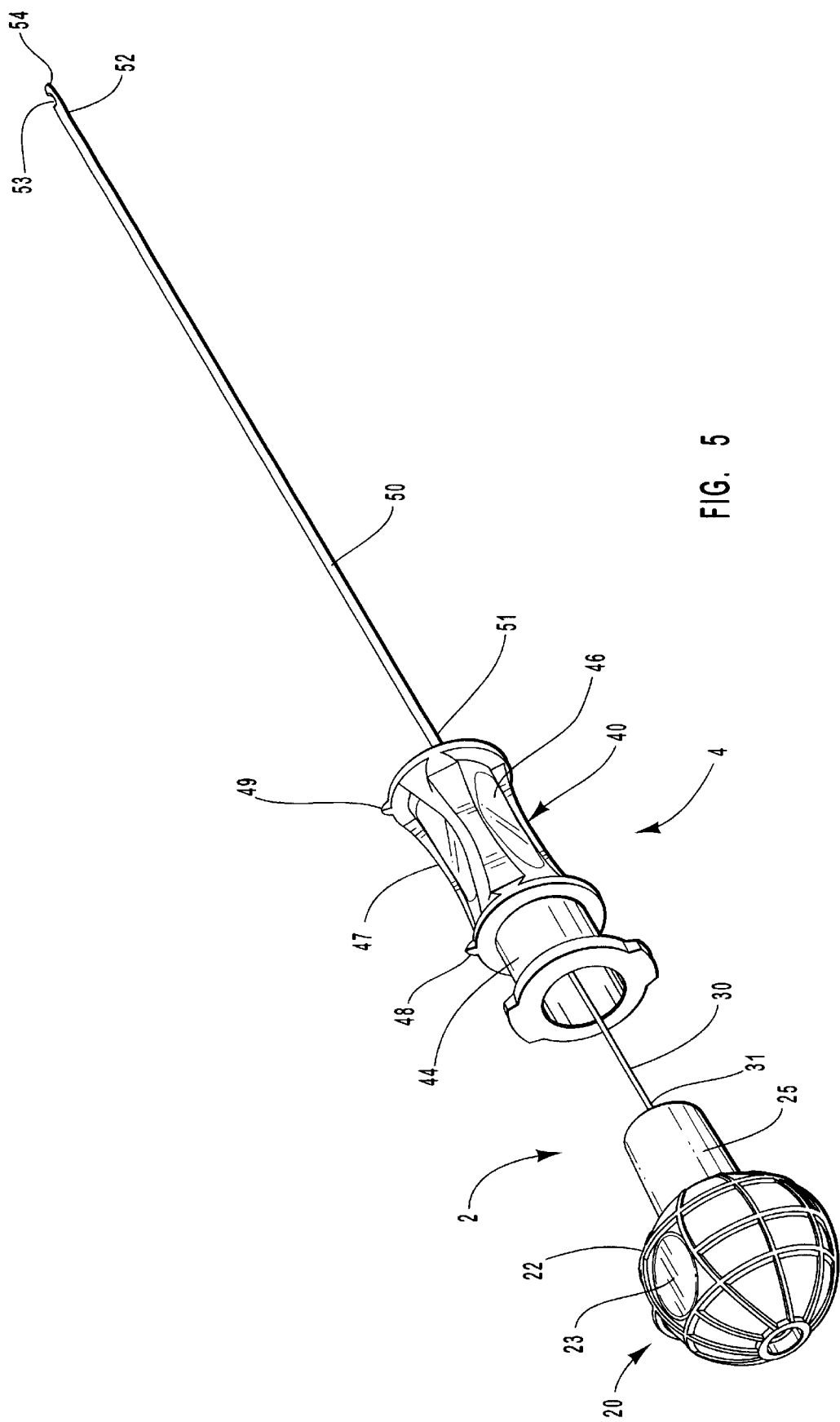
FIG. 5 shows a perspective view the stylet cap and stylet partially inserted and in alignment with the needle hub.

Stylet cap 20 has a generally spherical shape with raised portions 22 and flat areas 23 distributed throughout the surface of spherical stylet cap 20. The generally uniform shape of stylet cap 20 allows stylet cap 20 to be gripped with a conventional or uniform grip from almost any angle. Raised areas 22 and flat portions 23 of stylet cap 20 allow stylet cap 20 to be manipulated more easily, even when the user is wearing surgical gloves. Stylet cap 20 has a cap nose 25 component disposed around stylet 30 where stylet 30 communicates with stylet cap 20. Cap nose 25 is frusco-conical in shape with the broader base of the cone being adjacent to stylet cap 20. The diameter of nose 25 allows it to slide into and fit securely with hollow needle hub 40, as shown in FIG. 5. Stylet cap 20 and needle hub 40 create a pressure fit that allows stylet 30 to be rotated around its access and still be secured by pressure fit with needle hub 40. Stylet cap 20 does not need to be rotated to a particular orientation to create the pressure fit.

Stylet component 2 of the present invention offers several advantages. First, stylet 30 reinforces needle 50 as needle 50 is being inserted positioned or retracted. Second, as mentioned above, stylet 30 closes side port 53 of needle 50. Occlusion of site port 53 is a particular problem when stylet 30 is being repositioned during the procedure. Also, it is possible for side port 53 to cause trauma to the dura if side port 53 is left open during insertion. Additionally, the stylet also indicates whether needle 50 has been bent upon withdrawal.

In addition to the advantages above, stylet 30 of the present invention provides a stylet cap 20 that makes it easier to see and manipulate the stylet than prior art stylets cap. Stylet 30 reduces the likelihood that the anesthesiologist will mishandle or fumble with the stylet and thereby reduces the likelihood of unnecessarily traumatizing tissue, reduces the likelihood of headache due to a decrease in pressure of cerebral spinal fluid, and may save the anesthesiologist time. For example, during the procedure, the anesthesiologist may need to withdraw and reinsert needle 50 until he or she can obtain a backflow of spinal fluid through needle 50 into the needle hub 40. When this backflow is observed, the anesthesiologist may need to promptly reinsert stylet component 2 to occlude side port 53. Stylet cap 20 of the present invention facilitates the anesthesiologist's efforts to respond promptly, once the anesthesiologist verified spinal fluid flow through needle 50. Stylet cap 20 provides improved handling of stylet 30 and allows stylet 30 to be more quickly positioned and stylet 30 does not have to be aligned in a particular position relative to needle hub 40, like prior art devices.

Stylet 30 slides inside hollow needle 50 through needle hub 40 until stylet cap 20 contacts needle hub 40. The nose 25 of the stylet cap 20 slides into and contacts the interior walls of needle hub 40 creating a pressure fit between stylet nose 25 and the broad opening of needle hub 40. The spherical shape of stylet cap 20 obstructs broad opening 42 of needle hub 40.

As shown in FIG. 3, needle component 4 of the present invention further comprises needle 50 having a length and diameter suitable for spinal injection and having a rounded tip 54 and side port 53 opening. Needle 50 is hollow and has a rounded tip 54 on the injection (distal) end 52 and a needle hub 40 disposed around the syringe end (proximate end) 51. Needle 50 has two openings, a side port 53 opening near distal end 52, opening along the side of the needle, and an intake opening at proximate end 51.

Hollow needle hub 40 is disposed around proximate end 51 of needle 50. Needle hub 40 defines a funnel 41 having two openings, a first narrow opening 43 communicating with the needle intake opening and a wide opening 42 at the hub's proximate end. Nose 25 of stylet cap 20 can be inserted into wide opening 42 of the interior funnel in a pressure fit. The wide opening 42 has a shape corresponding to stylet cap nose 25 to allow such a pressure fit. In one embodiment, wide opening 42 is substantially cylindrical and tubular, allowing a frusco conical shape stylet cap nose 25 to form a pressure fit in wide opening 42. Needle hub 40 also provides an extended opening 44.

Needle hub 40 further comprises a finger grip 47 component disposed about interior funnel 41. Finger grip 47 has a plurality of sides and has a length and diameter which allows grip 47 to be easily manipulated between the thumb and forefinger. The sides of finger grip 47 can be slightly concave to facilitate handling. Additionally, needle hub 40 has magnifying window 46. Window 46 reveals the contents of the interior of hub 40 in magnified view. In one embodiment, the interior funnel 41 is magnified so that any fluid passing into or out of funnel 40 is more easily viewed by the user.

Needle hub 40 also provides a hub nose 45 at the distal end of hub 40 and disposed about the proximate end of needle 50. Needle hub nose 45 allows needle component 4 to be pressure fit with the proximate opening 62 of introducer component 6. In one embodiment, hub nose 45 is cross-shaped. Needle hub 40 also provides side port indicators 48 and 49. Side port indicators 48, 49 are raised portions of the needle hub 40 that correspond with the relative position of side port 53, so that orientation of side port 53 can be known when side port 53 is not in view. This allows the user to remain aware of the direction of the release or uptake of fluid through side port 53. In the preferred embodiment, the side port indicators 48, 49 are raised from the surface of the needle hub to provide visual and/or tactile and a verification of side port 53 orientation, as shown in FIG. 6.

Needle 50 conducts the flow of liquid from the syringe into the tissues and from the tissues into the syringe. Needle hub 40 allows needle 50 to be manipulated more easily. Needle 50 fits or slides through the hollow introducer hub 60 and through the introducer 70. Needle nose 45 forms a pressure fitting with a wide opening 62 of introducer hub 60.

As shown in FIG. 4, introducer component 6 of the present invention further comprises introducer 70 having a length and diameter suitable for spinal insertion and having a beveled tip. Introducer 70 is hollow and has a beveled tip 74 on the insertion (distal) end 72 and an introducer hub 60 disposed around the syringe end (proximate end) 71. Introducer 70 has two openings, a beveled tip 74 opening near distal end 72, and a base opening at the base of the introducer at the proximate end 71.

Hollow introducer hub 60 is disposed around proximate end 71 of introducer 70. Introducer hub 60 defines a funnel 61 having two openings, a first, narrow opening 63 at the distal end communicating with introducer 70 and a second wide opening 62 at the introducer hub's proximate end. Needle component 4 is releasably attached to introducer component 6 by means of needle hub nose 45 being inserted into wide opening 62 of interior funnel 61 in a pressure fit. Thus, wide opening 62 has a shape corresponding to needle hub nose 45 to allow such a pressure fit.

Figure 8:
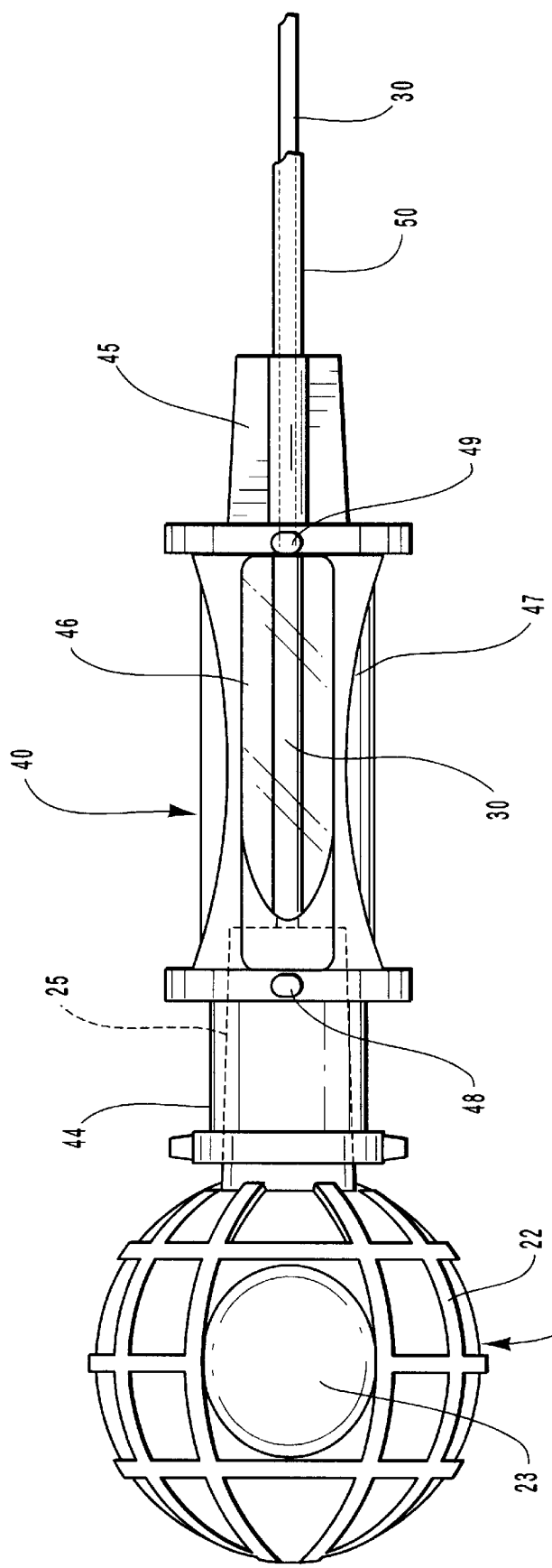
FIG. 8 shows the needle hub with a magnifying window showing the stylet in magnified view.

Introducer component 6 further comprises a finger grip 67 disposed about interior funnel 61. Finger grip 67 has a plurality of sides and has a length and diameter which allows finger grip 67 to be easily manipulated between the thumb and forefinger. The sides of finger grip 67 can be slightly concave to facilitate handling. Additionally, a magnifying window 66 may be disposed within introducer finger grip 67. Magnifying window 46 reveals the contents of interior funnel 61 of introducer hub 60 in magnified view, such that any fluid passing into or out of the magnified area of interior funnel 61 is more easily viewed by the user, as shown in FIG. 8.

Introducer hub 60 also provides a hub nose 65 at the distal end of the hub 60, disposed about proximate end 71 of introducer 70. Introducer hub nose 65 allows introducer 70 to be realeasably attached with a pressure fit to a protective sheath. In one embodiment, hub nose 65 has a cross-form shape section. Introducer hub 60 also provides bevel tip indicators 68, 69. Bevel tip indicators 68, 69 are a raised portion of the introducer hub 65 that correspond to the position of bevel tip 74 so that the position of bevel tip 74 can be known when bevel tip 74 is otherwise not visible. This allows the user to remain aware of the direction and angle of the cutting performed by bevel tip 74. In the preferred embodiment, bevel tip indicators 68, 69 are raised from the surface of the problem to provide visual and/or tactile verification of bevel tip 74 position, as shown in FIG. 7.

EXAMPLE

In one embodiment of the present invention, a spinal anesthetic delivery device comprises three components. A sharp, hollow introducer component a few centimeters in length that is used to puncture the skin, a more blunt hollow needle component that is several centimeters in length that is slideably disposed within the hollow introducer to allow the caregiver to delicately pierce the dura membrane, and a stylet component that is slideably disposed within the introducer to selectively occlude the needle and control the flow of fluid therein. The introducer and needle components both have relatively small transparent hubs on their proximate ends. The hubs act as handles or grips to facilitate manipulation of the introducer and needle and allow the caregiver to view fluids passing into or out of them.

Using the present invention, a care giver administers a lumbar puncture procedure following the steps typically used in procedures well-known in the art, but includes the advantageous steps of verifying the position of the side port and orienting the side port using side port indicators and the step of verifying the return of CSF and other fluids passing through the needle hub through the magnified window in the hub. Thus, one embodiment of the present invention, a method for spinal anesthesia comprises the steps of: placing the patient receiving the procedure in the lateral decubitus position on the edge of the bed with the patient's back exposed to the caregiver carrying out the procedure; placing the patient in a fetal like knees to chest position with the head supported so that the head and spine are parallel to the bed; locating and identifying the injection site along the spine; anesthetizing the patient's skin in preparation for inserting an introducer and spinal needle; inserting the introducer at the marked puncture point; advancing the needle slowly through the introducer until the dura membrane is breached; visually and tactually verifying the orientation of side port as the needle is advanced using side port indicators; withdrawing the stylet disposed within the needle, after the dura membrane is pierced, as the needle is advanced; verify the presence of CSF flowing back through the needle hub by viewing CSF through the magnified window on the needle hub; visually and tactually verifying the orientation of side port for delivery of the drug; injecting the anesthetic through the needle to induce the anesthetic block; withdrawing the needle and introducer without replacing the stylet; and dressing the puncture site with a bandage.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed is:

1. A spinal needle hub system comprising:
   an introducer-hub component, wherein the introducer-hub component is fixably coupled to a proximal end of an introducer having a distal beveled edge, and wherein the introducer-hub component includes at least one indicator that provides visual and tactual verification of the orientation of said distal beveled edge to a user;
   a needle-hub component that is selectively coupled to the introducer-hub component, wherein the needle-hub component is fixably coupled to a proximal end of the needle, and wherein the needle-hub component includes at least one indicator that provides visual and tactual verification to a user; and
   a stylet-hub component that is selectively coupled to the needle-hub component, wherein the stylet-hub component is fixably coupled to a proximal end of a stylet.

2. A spinal needle hub claim 1, wherein at least one of (i) the introducer-hub component and (ii) the needle-hub component includes a transparent portion to indicate fluid flow.

3. A spinal needle hub system as recited in claim 1, wherein the at least one indicator of the needle-hub component is configured for alignment with the at least one indicator of the introducer-hub component.

4. A spinal needle hub system as recited in claim 1, wherein at least one of (i) the introducer-hub component and (ii) the needle-hub component includes a magnifying window.

5. A spinal needle system comprising:
   an introducer having channel extending from a proximal end of the introducer to a distal beveled end of the introducer;
   a needle having a channel extending from a proximal end of the needle to a distal end of the needle, wherein the needle is configured to selectively extend through the channel of the introducer;
   a stylet having a proximal end and a distal end, wherein the stylet is configured to selectively extend down the channel of the needle; and
   a three-part hub system having a transparent portion to indicate fluid flow,
   wherein the three-part hub system comprises:
   (i) an introducer-hub component, wherein the introducer-hub component is fixably coupled to the proximal end of the introducer, and wherein the introducer-hub component includes at least one indicator that provides visual and tactual verification of the orientation of said introducer's distal beveled edge to a user;
   (ii) a needle-hub component that is selectively coupled to the introducer-hub component, wherein the needle-hub component is fixably coupled to the proximal end of the needle, and wherein the needle-hub component includes at least one indicator that provides visual and tactual verification to the user; and
   (iii) a stylet-hub component that is selectively coupled to the needle-hub component, wherein the stylet-hub component is fixably coupled to the proximal end of the stylet.

6. A spinal needle system as recited in claim 5, wherein the at least one indicator of the needle-hub component is configured for alignment with the at least one indicator of the introducer-hub component.

7. A spinal needle system as recited in claim 5, wherein at least one of (i) the introducer-hub component and (ii) the needle-hub component includes a magnifying window.

8. A spinal needle system as recited in claim 5, wherein the distal end of the needle is tapered.

9. A spinal needle system as recited in claim 5, wherein the needle includes an aperture near the distal end.

10. A spinal needle system as recited in claim 9, wherein a portion of the stylet occludes the aperture when the stylet is in a fully extended position.

11. A spinal needle system as recited in claim 9, wherein the stylet does not occlude the aperture when the stylet is in a retracted position.

12. A spinal needle system as recited in claim 5, wherein the distal end of the introducer includes a blade.

13. A spinal needle system as recited in claim 12, wherein the at least one indicator of the introducer-hub component provides visual and tactual verification to the user as to a direction and angle of a cut performed by the blade.

14. A spinal needle system as recited in claim 5, wherein the stylet-hub component is pivotally coupled to the needle-hub component in any position within a 360° pivot range.

15. A spinal needle kit comprising:
    an introducer having channel extending from a proximal end of the introducer to a distal beveled end of the introducer;
    a needle having a channel extending from a proximal end of the needle to a distal end of the needle, wherein the needle is configured to selectively extend through the channel of the introducer;
    a stylet having a proximal end and a distal end, wherein the stylet is configured to selectively extend down the channel of the needle; and
    a three-component hub system that is configured to be interconnected, wherein the hub system has a transparent portion to indicate fluid flow and comprises:
    (i) an introducer-hub component that includes at least one indicator to provide visual and tactual verification of the orientation of said introducer's distal beveled end to a user;
    (ii) a needle-hub component that is fixably coupled to the proximal end of the needle, and wherein the needle-hub component includes at least one indicator that provides visual and tactual verification to a user; and
    (iii) a stylet-hub component that is fixably coupled to the proximal end of the stylet.

16. A spinal needle kit as recited in claim 15, wherein the at least one indicator of the needle-hub component is configured for alignment with the at least one indicator of the introducer-hub component.

17. A spinal needle kit as recited in claim 15, wherein at least one of (i) the introducer-hub component and (ii) the needle-hub component includes a magnifying window.

* * * * *